(12) United States Patent
Bennett et al.

(10) Patent No.: US 10,345,233 B2
(45) Date of Patent: Jul. 9, 2019

(54) OPTICAL MEASURING DEVICE HAVING PHOTONIC CHIP WITH INTERFEROMETER AND PHASE ADJUSTER SET FOR MINIMIZING SIGNAL FROM INTERFERENCE REGION

(71) Applicant: KABUSHIKI KAISHA TOSHIBA, Tokyo (JP)

(72) Inventors: Anthony John Bennett, Cambridge (GB); David Julian Peter Ellis, Cambridge (GB); Andrew James Shields, Cambridge (GB); Thomas David Meany, Cambridge (GB)

(73) Assignee: Kabushiki Kaisha Toshiba, Tokyo (JP)

( * ) Notice: Subject to any disclaimer, the term of this patent is extended or adjusted under 35 U.S.C. 154(b) by 122 days.

(21) Appl. No.: 14/861,606

(22) Filed: Sep. 22, 2015

(65) Prior Publication Data

US 2016/0356708 A1 Dec. 8, 2016

(30) Foreign Application Priority Data

Jun. 3, 2015 (GB) .................................. 1509655.5

(51) Int. Cl.
*G01N 21/45* (2006.01)
*G02F 1/01* (2006.01)
(Continued)

(52) U.S. Cl.
CPC ............. *G01N 21/45* (2013.01); *G02B 6/125* (2013.01); *G02F 1/0147* (2013.01);
(Continued)

(58) Field of Classification Search
CPC ............. G01N 21/45; G01N 2021/458; G01N 2201/08; G02B 6/125; G02B 2006/12159;
(Continued)

(56) References Cited

U.S. PATENT DOCUMENTS 2,924,142 A 2/1960 Nomarski
4,515,430 A 5/1985 Johnson
(Continued)

FOREIGN PATENT DOCUMENTS

EP 0 591 912 A2 4/1994
JP 11-37718 2/1999
(Continued)

OTHER PUBLICATIONS

Combined Search and Examination Report issued by the United Kingdom Intellectual Property Office dated Nov. 23, 2015, for GB Application No. GB1509655.5.

*Primary Examiner* — Hwa Andrew Lee
(74) *Attorney, Agent, or Firm* — Finnegan, Henderson, Farabow, Garrett & Dunner, L.L.P.

(57) ABSTRACT

An optical measuring device for measuring a measurement region, the optical device comprising a photonic chip with an interferometer defined on said chip, said interferometer comprising first and second waveguides on said photonic chip and an interference region, wherein the first and second waveguides carry signals from the interference region to the sample region and back to the interference region, the device further comprising a phase adjusting unit configured to vary a phase difference between the signals in the first and second waveguides reflected by the measurement region.

13 Claims, 6 Drawing Sheets

(51) Int. Cl.
*G02B 6/125* (2006.01)
*G02B 6/293* (2006.01)
*G02B 6/12* (2006.01)

(52) U.S. Cl.
CPC ... *G01N 2021/458* (2013.01); *G01N 2201/08* (2013.01); *G02B 6/29352* (2013.01); *G02B 2006/12121* (2013.01); *G02B 2006/12123* (2013.01); *G02B 2006/12159* (2013.01)

(58) Field of Classification Search
CPC ...... G02B 6/29352; G02B 2006/12121; G02B 2006/12123; G02F 1/0147
See application file for complete search history.

(56) References Cited

U.S. PATENT DOCUMENTS

| | | |
|---|---|---|
| 4,941,744 A | 7/1990 | Yokokura et al. |
| 5,396,328 A | 3/1995 | Jestel et al. |
| 2002/0015155 A1 | 2/2002 | Pechstedt et al. |
| 2006/0216200 A1* | 9/2006 | Nagatomo ........... G01N 21/774 422/68.1 |
| 2015/0131106 A1 | 5/2015 | Pruessner et al. |

FOREIGN PATENT DOCUMENTS

| | | |
|---|---|---|
| JP | 2006-23409 | 1/2006 |
| WO | WO 2005/114094 A1 | 12/2005 |

\* cited by examiner

OPTICAL MEASURING DEVICE HAVING PHOTONIC CHIP WITH INTERFEROMETER AND PHASE ADJUSTER SET FOR MINIMIZING SIGNAL FROM INTERFERENCE REGION

FIELD

Devices in accordance with embodiments are concerned with the field of optical sensing.

BACKGROUND

In the field of optical sensing there is a need to accurately measure or detect an optical difference in an object that may be related to its refractive index, emission properties, thickness or position.

BRIEF DESCRIPTION OF THE FIGURES

Devices in accordance with embodiments of the present invention will now be described with reference to the following figures in which.

DETAILED DESCRIPTION OF THE FIGURES

In an embodiment, an optical measuring device is provided for measuring a measurement region, the optical device comprising a photonic chip with an interferometer defined on said chip, said interferometer comprising first and second waveguides on said photonic chip and an interference region, wherein the first and second waveguides carry signals from the interference region to the sample region and back to the interference region, the device further comprising a phase adjusting unit configured to vary a phase difference between the signals in the first and second waveguides reflected by the measurement region.

The above arrangement is provided on a photonic chip and this allows the entire measurement system to be provided on a single chip.

In one embodiment, the measurement region comprises a first region and a second region, the signal in the first waveguide being reflected by the first region and the signal in the second waveguide being reflected by the second region, wherein the phase adjusting unit is configured to adjust the phase such that there is maximum interference at the interference region when the reflectance properties of the first region and the second region match. The reflectance properties may be any properties that affect the signal that is reflected back into the first and second waveguides, for example, the distance of a reflective surface from the first and/or second waveguides, the reflectance properties of an actual reflective surface or the absorption properties of a material through which the signal is reflected.

By maximising the interference in this way, the output from the interference region can be controlled to follow a specific exit path or suppress the use of a particular exit path. In an embodiment, if the interference is maximised to suppress output along a predetermined path from the interference region, then variations between the first and second region manifest themselves as quite significant changes in the output along the path where the signal is suppressed when the first and second regions are matched.

In a further embodiment, the optical measuring device, further comprises an input waveguide and an output waveguide defined on said photonic chip, the input waveguide being adapted to pass a light signal to said interference region such that the light signal propagates along the first and second waveguides after the interference region, the output waveguide being configured to carry a signal from the Interference region after it has been reflected by the measurement region, the amount of signal transferred to the output waveguide from the input waveguide being controlled by the phase adjusting unit. A light source may be attached to the input waveguide, for example, the light source could be laser bonded to the end of the chip of actually within the waveguide.

In one mode of operation, where the measurement region comprises a first region and a second region, the signal in the first waveguide being reflected by or through the first region and the signal in the second waveguide being reflected by or through the second region, wherein the phase adjusting unit is configured to adjust the phase such that the signal transferred to the output waveguide is minimised when the optical properties of the first region and the second region with respect to the signals in the first and second waveguides match. Thus, changes in the optical properties between the first and second regions can be detected by monitoring the signal in the output waveguide.

In a further embodiment, a detector is provided to receive the output from the output waveguide.

In a different mode of operation, the optical measuring device further comprises a controller adapted to control the phase adjusting controller to minimise the output signal in the output waveguide and determine the phase adjustment applied for minimising the signal in the output waveguide. In this arrangement, the phase adjustment is varied to minimise the signal in the output waveguide and the phase adjustment applied is used as a measure of the differences between the first and second regions. For example, in one embodiment, the phase difference that needs to be applied when the first and second regions are matched is determined as a reference value and then all other phase adjustments are measured with respect to this reference.

In a further embodiment, the input waveguide and the first waveguide are defined by a single continuous waveguide and the output waveguide and the second waveguide are defined by a single continuous waveguide, wherein, in the interference region, the continuous waveguides are in close proximity such that the evanescent fields from the guided modes in the continuous waveguides overlap. In a further arrangement the input waveguide and the second waveguide are defined by a single continuous waveguide and the output waveguide and the first waveguide are defined by a single continuous waveguide, wherein, in the interference region, the continuous waveguides cross one another. In a yet further arrangement, the input waveguide, the output waveguide, the first waveguide and the second waveguide are separate waveguides and wherein the interference region comprises a multimode coupler.

As noted above, the optical measuring device is provided on a photonic chip. The photonic chip may have multiple elements supported on a planar substrate. Such elements may include couplers, light sources, switches, heaters or detectors. In one embodiment, the materials used to define the waveguides are selected from a silicon oxide undoped cladding with a silicon oxide doped core or silicon oxynitride with higher index Nitride-rich core and lower index oxide rich cladding. In a further embodiment, the waveguide could also be semiconductor, ridge waveguide, a suspended bridge.

In an embodiment, the phase adjusting unit comprises a phase adjusting element on said photonic chip configured to vary the phase shift of light travelling along at least one of the first and second waveguides. The phase adjusting element on said photonic chip may be a heating element configured to heat part of the first and/or second waveguide.

Although devices in accordance with embodiments of the present invention may be used to determine differences in the reflective properties of the first and second regions, they may also be used to determined differences in the transmissive properties. In one embodiment, the measurement region comprising a first region and a second region, wherein the first region and the second region transmit radiation at the frequency of the Input optical signal, the device further comprising a mirror provided such that an optical signal transmitted through the first region is reflected from the mirror back into the first waveguide and a mirror provided such that an optical signal transmitted through the second region is reflected back from the mirror into the second waveguide. For example, the first region may be configured to contain a fluid and the second region may be configured to contain a fluid, the first and second regions being configured such that the physical path length of the optical signal through the fluids contained in the first and second regions is the same to allow variations in the refractive index to be determined between the fluid in the first region and the fluid in the second region.

In a further embodiment, the measuring device is configured as a microscope. Here, the device further comprises a movement stage configured such that the measurement region is moveable with respect to the first and second waveguides. The signal on the output waveguide here represents the difference between the first and second regions. The first and second regions will both change as the stage is moved.

The above examples have mainly related to the measurement of differences in the optical properties of the measurement region. However, the optical measuring device may be configured to measure the displacement of an object in said measurement region. In such an arrangement, a measurement stage (either mobile or non-mobile) is provided configured to position the object such that the displacement of the object in the measurement region causes a variation in the path length between the signals following the first waveguide and the second waveguide, the device further comprising a detector adapted to measure the signal in the output waveguide over time.

In a further embodiment, the optical measuring device is configured to measure the output from an optically activated quantum emitter, the optical measuring device further comprising a stage for supporting said quantum emitter in the measurement region such that said quantum emitter is coupled to the first waveguide, the phase unit configured to vary a phase difference between the signals in the first and second single to minimise the signal transferred from the input waveguide to the output waveguide. In this arrangement, the signal used to excite the quantum emitter is removed from the emission from the quantum emitter itself at the interference region. Hence, the signal from the quantum emitter can be easily observed and manipulated. In one embodiment, the signal from the quantum emitter in the output guide is coupled to a further photonic circuit comprising an arrangement of couplers, phase shifters, delays and detectors.

In a further embodiment, an optical measuring system is provided comprising a first optical measuring device and a second optical measuring device, the first optical measuring device comprising the above optical measuring device and the second optical measuring device comprising the above optical measuring device, wherein the output guide of the first optical measuring device and the output guide of the second optical measuring device are coupled at a coupler.

In an embodiment, the optical measuring device further comprises a variable loss element provided in at least one of the first and second waveguide, wherein the variable loss element is configured to vary the amplitude of the signal in said at least one of the first and second waveguide.

In a further embodiment, the first and second waveguides are single mode waveguides.

The interference region may be configured to divide the light signal passed to the Interference region unequally or equally.

In an embodiment, the light signal passed to the interference region is monochromatic.

In a further embodiment, a method of performing an optical measurement of a measurement region is provided, the method comprising providing a an optical measuring device comprising a photonic chip with an interferometer defined on said chip, said interferometer comprising first and second single mode waveguides on said photonic chip and an interference region, the method comprising passing signals from the interference region via said first and second waveguides to the measurement region and back to the interference region via the same first and second waveguides and varying a phase difference between the signals in the first and second single waveguides reflected by the measurement region.

Such a device can be designed and operated to make it sensitive to small optical differences in two objects acting as reflectors.

Devices in accordance with the above embodiment allow the optical measurement of small differences between a first region and a second region. For example, the first region may be a Test Area, which could be measured relative to some Reference Area (second region). Devices in accordance with this embodiment are sensitive to any difference in the light signal reflected by a sample, whether that be a change in amplitude, polarisation or phase of the signal caused by changes in position, refractive index, emission properties.

Figure 1:
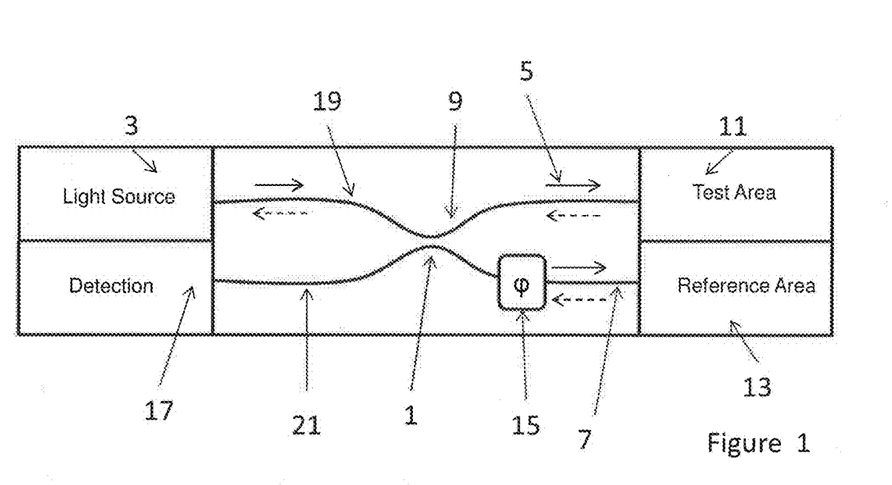
FIG. 1 is a diagram of an optical device in accordance with an embodiment.

FIG. 1 shows a schematic of a device in accordance with an embodiment of the present invention. Photonic chip 1 is provided having a first waveguide 5 and a second waveguide 7 exiting an interference region 9. The first waveguide 5 couples to a test area 11 and the second waveguide 7 couples to a reference area 13. In the embodiment, the photonic chip further comprises an input waveguide 19 that is coupled to a light source 3, and the light signal propagates along the input waveguide 19 to the interference region 9. An output waveguide 21 is provided between the interference region 9 and a detector 19.

In the device of FIG. 1, the input waveguide 19 and the first waveguide 5 are a single continuous waveguide and the output waveguide 21 and the second waveguide are a single continuous waveguide. The two continuous waveguides are shaped to define an optical coupler between them in the interference region 9.

An integral light source 3 is provided on the photonic chip and the chip is configured such that light from the light source 3 is coupled into the input waveguide 19. Input waveguide 19 is a single mode waveguide and propagation of light along input waveguide 19 progresses to the interference region 9.

At the interference region 9, optical modes in the two continuous waveguides overlap and hence the light signal travelling in the input waveguide 19 away from the light source 3 is split between the first waveguide 5 and the second waveguide 7. The light signal in the first waveguide then continues along the first waveguide until the termination of the first waveguide at the first region 11. Here the light signal is reflected from the first region 11 back into the first waveguide where it propagates towards the interference region 9 again as shown by the dotted arrow. The light signal which has transferred to the second waveguide 7 at the interference region 9 then propagates along the second waveguide 7 until the termination of the second waveguide at the second region 13. Here the light signal is reflected from the second region 13 back into the second waveguide where it propagates towards the interference region 9 as shown by the dotted arrow. From here on, the first region 11 will be referred to as the test area and the second region 13 will be referred to as the reference area.

When incident on the interference region 9, the light reflected from the test area 11 and the reference area 13 will interfere.

A phase shift component 15, which may be located in either or both of the first waveguide 5 or the second waveguide 7 is configured to cause a phase shift between the two light signals reflected from the test area 11 and the reference region 13 which ensures Interference at the interference region 9 preferentially directs the majority of the light back along the input waveguide 19. However, if there is incomplete destructive interference some light will propagate in output waveguide 21 towards optical detector 17.

Thus optical detector 17 can be used to measure the extent to which this destructive interference was achieved. This detector is particularly sensitive to small optical differences in the reflected signals from the Test area 11 and the Reference area 13.

In the case where the Test Area 11 and Reference area 13 are the same, and the path length from the interference region 9 to Test area 11 is equal to the path length from the interference region 9 to the Reference Area 13, then the light entering the input waveguide 19 from the light source 3 after reflection will be fully directed into the output waveguide 21.

Thus to minimise the light in the output waveguide 21, the phase shift element 15 must be set to impart a phase shift of pi/2 on each pass. In the arrangement shown in FIG. 1, the light travelling in the second waveguide 7 traverses the phase shift element before reaching the Reference Area 13 and on being reflected from this area 13, it will collect a total phase shift of pi. Thus interference at the interference region 9 will minimise the signal at the detector 17.

In an embodiment, the light source 3 is electrically controlled but may emit any form of light, possible examples being a laser or a light emitting diode. In an embodiment, the light source is located on the chip directly injecting photons into the input waveguide 19. Alternatively, it may be located in another place and light guided to the integrated photonic chip by means of an optical fibre.

In an embodiment, the photonic chip may be formed as part of an inherently stable and solid material system, such that the optical modes may be defined with ease. Possible methods of achieving this will be described later. The only condition is that the waveguides only support one optical mode at the energy of the injected photons and that it be interferometrically stable (that is, stable on the scale of a fraction of the photon wavelength). As an example, a device in accordance with an embodiment is able to vary the light coupled into the output waveguide by a factor known as the Extinction Ratio, ER (which is the maximum signal in output waveguide divided by the minimum signal in the output waveguide) by means of changing the phase shift element 15. In this embodiment, the phase stability should be a value of at least wavelength/ER or lower.

The interference region 9 on the chip allows the light entering the input waveguide 19 to be split between the first 5 and second 7 waveguides after passing through the interference region 9. Possible designs will be discussed later. In the embodiment discussed herein the interference region 9 comprises a coupler. This coupler should be unitary: that is, display low loss.

In this embodiment the phase change element 15 is also interferometrically stable and externally controlled, for instance by electrical means. In one embodiment, exemplified in a photonic chip material system, this can be a resistive wire (defined by standard photolithography) on the surface of the sample which locally changes the temperature as current is driven through it. It need only be able to introduce a phase change sufficient to minimise the light which couples to the output waveguide 21: this means it must be able to impart a phase change of $\pi$ on a single pass ($2\pi$ on passing back and forth through the second waveguide 7). By symmetry this phase change element may alternatively, or additionally, be located in the first waveguide.

In this embodiment, the output of the first waveguide is coupled to Test area 11 and the output of the second waveguide is coupled to Reference area 13. The Test 11 and Reference 13 areas are, in one embodiment, in the plane orthogonal to the direction of propagation of the light propagating in the first 5 and second 7 waveguides, positioned so that some reflected or scattered light from these areas is coupled back into the first and second waveguides where it propagates towards the interference region. In one example the Test/Reference areas are very close to the end of the first and second waveguides. In the event that the Test area 11 and Reference area 13 are identical, or at least reflect or scatter the same light, the phase shifter 15 is set to minimize the signal that reaches the optical detector 17. The single optical modes of the optical chip will define the extent of the Test 11 and Reference 13 areas illuminated.

In some applications, the detector may be a "single photon detector", such as Avalanche Photo-diode, superconducting single pixel detector or similar. However, in some applications larger intensities may be acquired and a Photo-Multiplier Tube, photodiode or CCD may be used. This detector 17 may be integrated onto the chip or located elsewhere with light from the second waveguide 7 coupled to the detector 17 by means of an optical fibre.

Figure 2:
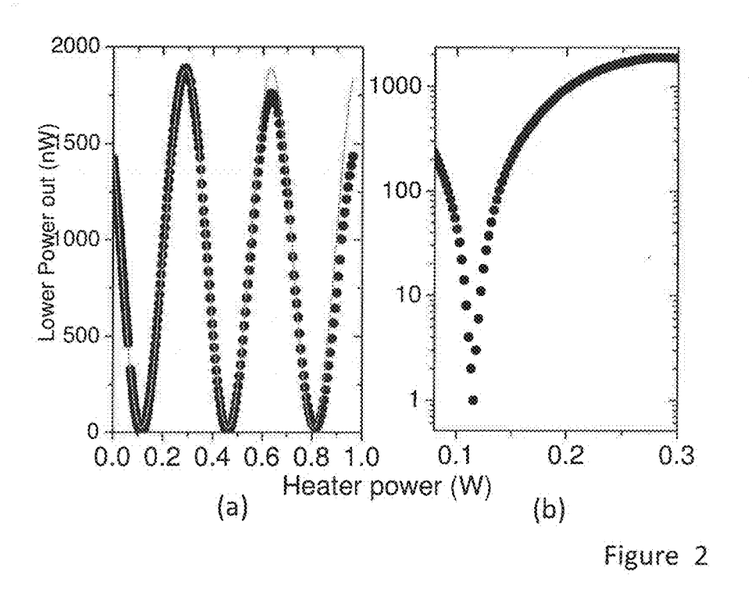
FIG. 2 is experimental data showing the basic operation with a resistive heater providing the phase change, (left) a large range of data on a linear scale to show the sinusoidal change in the output power and (right) the same data on a logarithmic scale to illustrate the strong suppression of the laser at 0.116 W heater power.

FIG. 2 shows experimental data from a device in accordance with an embodiment. In this case the light source 3 was a CW laser emitting at 940 nm, the photonic chip comprised doped Silicon Oxide waveguides embedded in undoped silicon oxide and the detector 17 was a Silicon photodiode.

To provide an optically similar Test area 11 and Reference area 13, a GaAs/AlAs Bragg mirror on a GaAs substrate was used, the structure was pushed up to the end of the integrated chip at right angles to the mode propagating along the first 5 and second 7 waveguides.

FIG. 2(a) shows the intensity of light in the output waveguide as a function of the phase shift applied by the phase shifting element 15. In this case the phase shift is proportional to the heater power used to drive the phase shift element 15. As constructive and destructive interference occurs, the light intensity in the output waveguide 21 follows a sinusoidal variation. The apparent non-zero phase shift at zero Heater Power is a result of a small difference in path lengths of the first and second waveguides which occurred during fabrication, which has no impact on the performance of the devices in accordance with embodiments of the invention.

At heater powers where the light in the output waveguide is minimised, an example of which is shown in the right hand figure at 0.116 W heater power, there is maximum destructive interference at the interference region 9. At the minimum signal, the light at the output waveguide is reduced by a factor of 2600. Near to this minimum any small change in the phase shift in the signal propagating in the first and second waveguides leads to a large change in signal in the output waveguide: the sensitivity to small changes in phase is maximised. FIG. 2(b) shows the data from FIG. 2(a) expanded at one of the minima shown in FIG. 2(a). For the demonstration in FIG. 2 the phase shift is introduced by changing the phase shift element by heating, but could just as easily be caused by a change in the light reflected at the Test area 11.

In the above described embodiment, there has been no restriction on the splitting ratio of the coupler. In some embodiments the coupler may be a 50/50 coupler. However, in general the intensity reflection (R) and intensity transmission (T) coefficients may take any value. This is because the path from the input waveguide 19 to the first waveguide 5 and then from the first waveguide 5 to the output waveguide 21 scales the light intensity by a factor RT, and the path from the first waveguide 19 to the second waveguide 7 and then from the second waveguide 7 to the output waveguide 21 scales the light intensity by a factor TR. In some embodiments, there may be some practical advantages to choosing a coupler with T greater than 50%: for example, when fluorescence or emission from a source in the Test area is being detected, it will be advantageous to have as many photons as possible emitted by this source reach the output waveguide 21.

Figure 3:
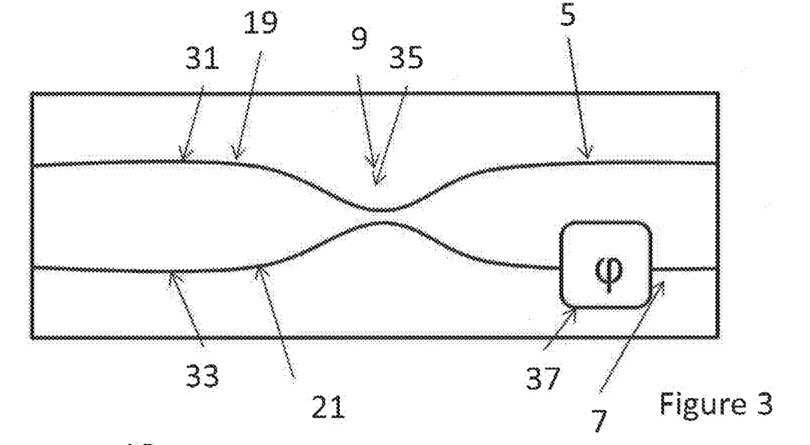
FIG. 3 is a diagram of a coupler which may be used in an optical device in accordance with an embodiment.
Figure 4:
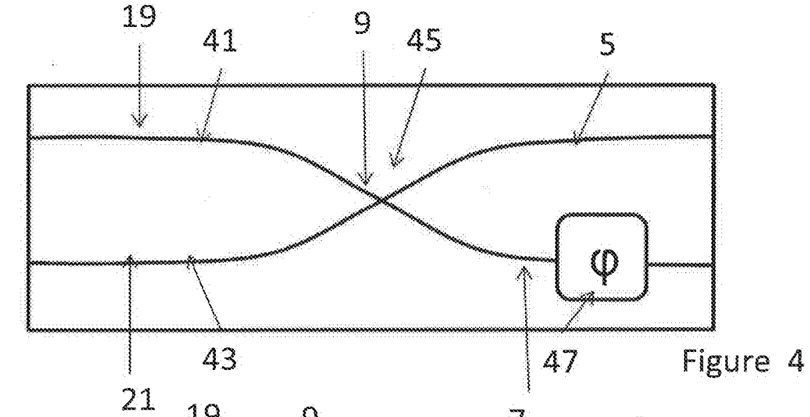
FIG. 4 is a diagram of an alternative coupler design to the type shown in FIG. 3.
Figure 5:
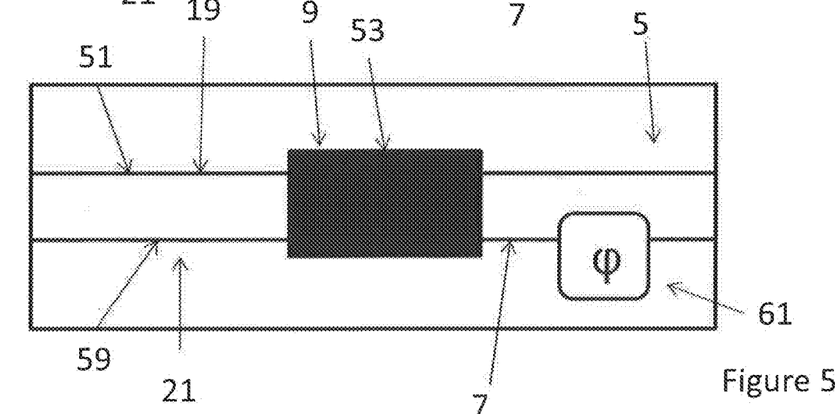
FIG. 5 is a diagram of an alternative coupler design to the types shown in FIGS. 3 and 4.

FIGS. 3 to 5 show 3 possible coupler designs in accordance with embodiments of the present invention. The designs shown in FIGS. 3 to 5 are realised in a photonic chip. Optical waveguides act as channels through which light can be routed, ideally with little loss. Confinement of the optical path occurs along a core region by means of total internal reflection. This is possible, through the design of the guide, such that the "core" region has a higher effective refractive index than the surrounding ("cladding") layers.

This necessary refractive index can be realised in a number of ways and using a number of materials systems including dielectrics (such as $SiO_2$, $SiO_xN_y$, $Si_3N_4$), polymers, silicon-on-insulator, $Li_3NBO$ and III-V materials such as InP and GaAs. The waveguides may be defined using standard optical lithography or electron beam lithography. Materials may be grown using a range of techniques including chemical vapour deposition (CVD); plasma enhanced chemical vapour deposition (PECVD) or Flame hydrolysis deposition (FHD) to name a few, without wishing to limit the invention.

The physical dimensions of the core determine the properties of the waveguide in terms of the number of optical modes which it will support, and the area it probes on the "Test Area". This is a function of both the refractive index profile of the system and the wavelength of the light to be guided. In one embodiment an etched silicon oxynitride dielectric core layer is provided, surrounded by silicon dioxide under- and overcladding layers. Silicon oxynitride can have refractive index varying from 1.5-2.0 at 300K, depending on the oxygen/nitrogen proportion in the material. Dependant on the refractive indices used, the mode may support a single optical mode at 900 nm if the waveguide has a cross sectional area of only 1.5×1.5 microns.

However, in some embodiments a lower refractive index contrast is used and greater waveguide dimension so that the mode is better matched to standard optical fibres' mode size (typically 5-6 micron diameter at 900 nm, and of circular cross section), facilitating connection of the modes on the chip to external light sources and detectors.

In a further embodiment, the waveguides are spaced at 250 microns as this is a standard spacing for fibre-optical arrays which may be used to connect to waveguides A and B. A final dimension is the overall length of the photonic chip, which, in an embodiment, is sufficient to hold the coupler and heater (provided the light source and detectors are located off the chip). This length may be on the scale of a few mm up to a few cm.

In some applications the positions of either the waveguides may be fixed with respect to the Test 11 and Reference Areas 13, or with respect to the Light source and Detector. This could be achieved through the use of adhesive, mechanical positioning or by some other method. This will make the device robust for future use.

Waveguide structures may be defined in a number of ways:

1. Through the deposition of flat $1^{st}$ cladding and overlaying flat core layer with higher refractive index and the subsequent etching of the core to define the width of the "core" and final deposition $2^{nd}$ cladding layer. This method creates guides of rectangular cross-section with step-like refractive index variation. Materials used in such cases include silicon-on-insulator, and dielectrics such as silicon dioxide, silicon nitride and silicon oxynitride. In these cases, refractive index contrast may be achieved, for example, by using dielectrics with different stoichiometry, or by doping one of the layers to modify the refractive index.

2. By introducing some physical change within a layer post-growth, by selectively exposing part of the structure to some external stimulant. For example, one could use an ultraviolet laser, focussed to a point within a Ge-doped layer of $SiO_2$ to create a controlled, semi-permanent increase in refractive index. By tracing the laser through the $SiO_2$ layer a waveguide can be defined. This creates guides of circular/oval cross section with smoothly varying refractive index variation.

3. By depositing and/or patterning structures on top of the grown structure in order to modify the effective refractive index of the whole sample, for example, etching a ridge on the surface.

Waveguide couplers are the analogue of a free space beam-splitter. They allow an incident beam of photons to be split between a given number of output paths in some pre-determined ratio. Examples of couplers are in FIGS. 3-5.

In the case of the directional coupler FIG. 3, two waveguides 31, 33 are brought into close proximity at region 35 such that the evanescent field from the guided mode in each channel 31, 33 overlap. This allows the energy confined within the system to oscillate periodically between the two waveguides 31, 33 at region 35. By controlling the length over which this interaction can occur, one can precisely control the coupling ratio of the device. The phase varying element 37 can be provided in one or both of the waveguides as explained with reference to FIG. 1.

In FIGS. 1, 6-10 the coupler is drawn as a directional coupler, without loss of generality. Possible methods to achieve a phase shift in the device will be discussed, but other methods may be possible. FIG. 4 shows an X coupler, which achieves a similar result to that described with reference to FIG. 3, but here the two waveguides 41, 43 physically intersect at region 45. The angle at which the guides meet determines the ratio with which the light is split. The phase varying element 47 can be provided in one or both of the waveguides as explained with reference to FIG. 1.

A third type of coupler is the multi-mode interference coupler as shown in FIG. 5. Here a typically single mode input waveguide 51 will launch into a much wider section 53 which can support multiple optical modes. The incident field will excite some of these modes, which then evolve as they propagate down the multi-modal waveguide element 53. At certain points along the structure's length, these multiple modes will interfere to create a copy (or multiple copies) of the incident launch field. If the first and second waveguides 55, 57 are located to coincide with these points, one is able to extract multiple copies of the launch field and hence realise a coupler. The phase varying element 61 can be provided in one or both of the waveguides as explained with reference to FIG. 1.

Reversible phase shifts in waveguide systems are realised by modifying the local refractive index of part of the structure. In one embodiment, this can be achieved by: physically heating a small length of waveguide using a resistive heater through which current is passed; strain, induced by applying some force to the waveguide structure also allows for the realisation of a phase shifting device. Once the external heat or pressure is removed the system will gradually return to its original state. In materials which exhibit an electro-optic effect, a change can be realised by applying an electric field across a length of waveguide.

An alternative medium which could be employed as a phase shifter are chalcogenide glasses. These materials' physical state can be switched between amorphous and crystalline through the application of heat. In each state, the material exhibits different optical properties, such as refractive index. Once tuned, the external heat source can be removed and the phase shifting element will be fixed in position. Should further adjustment be required, heat can again be applied to further modify, or reverse previous changes in the material.

Figure 6:
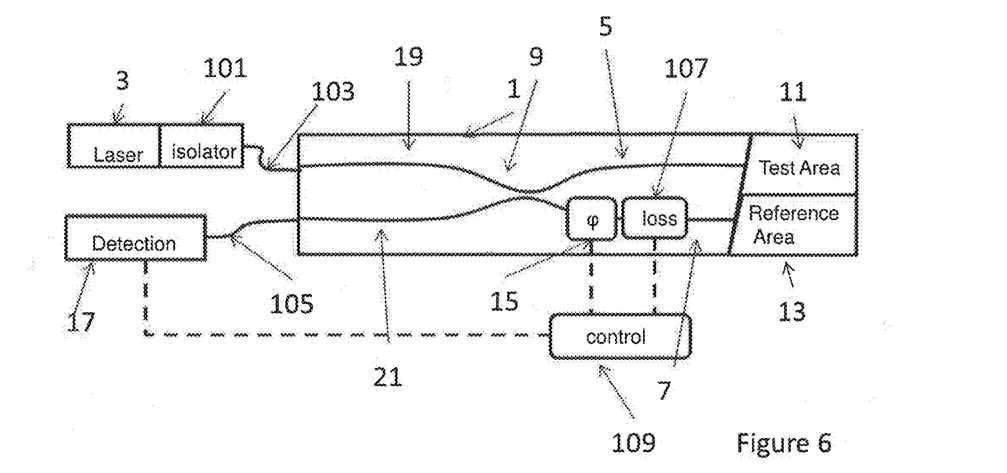
FIG. 6 shows a diagram of the above apparatus where the addition of an optical isolator prevents light reflected by the device re-entering the light source which may affect its operation, for instance if it is a laser.

FIG. 6 shows a device in accordance with a further embodiment incorporating some optional additional elements. To avoid any unnecessary repetition, like reference numerals will be used to denote like features.

In some applications an optical isolator 101 is provided between the light source 3 and photonic chip 1. An example is when the light source 3 is a Laser and the reflected light may affect the lasing operation of the laser.

In FIG. 6, optical fibres 103, 105 are shown leading from the photonic chip to the light source and detector. In some embodiments the components around the photonic chip 1 (the light source 3, detector 17, test area 11, reference area 13) are directly coupled to the photonic chip in others they may be coupled to the photonic chip 1 via optical fibres. In the figures, even if no optical fibres are shown, such fibres may still be present in the actual device.

In a further embodiment, a variable loss element 107 in the second waveguide 7 may also be provided. In this case, most generally, control of the phase and amplitude of the light reflected by the reference area 13 may be modulated to ensure the light interferes to minimise the light reaching the output waveguide 21.

Additionally, the reference area or reference reflector 13 may be integrated onto the chip 1: for instance by depositing a layer of gold on the end of the second waveguide. Whereas, the test area 13 may be of a different type: i.e. a sample to be measured. In this case both test area 11 and reference reflector 13 are likely to have different amplitude reflection coefficients. Optimisation of the variable loss element 15 ensures that maximally destructive interference can still occur between the reflected light beams in the interference region 9.

In a further embodiment, a control system 109 is provided which can change the phase shift element 15, variable loss element 107 and read from the detection element 17 to minimise the signal at the detection element 17.

In such an arrangement, the signal applied to the phase change element at which the interference is maximised is used as an Indication of the change between the reference area 13 and test area 11.

FIG. 6 also illustrates that the lengths of first waveguide 5 and second waveguide 7 that is from the coupler to the test area 11 and from the coupler to the reference area 13 may have the unequal optical length. When this is the case, light passed from the input guide 19 to the output guide 21 can be made to destructively interfere regardless of its wavelength. Thus there is no restriction on the spectral width of the light from the light source. However, in an embodiment where the lengths of the first 5 and second 7 waveguides are not equal the spectral width of the light source should be chosen to allow propagation into the output guide to be minimised.

Figure 7:
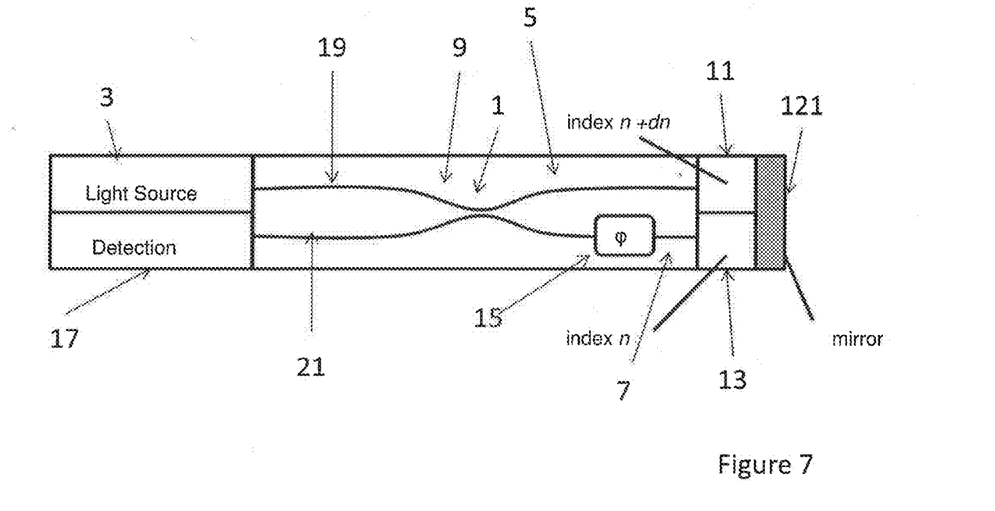
FIG. 7 is a device for measuring the refractive index difference of fluids in two channels at the outputs of the two ports.

FIG. 7 is a schematic of a device that is used to sense small changes in refractive Index between the test area 11 and reference area 13. In this case the first 5 and second 7 waveguides are incident on sections of a partially transparent material, behind which lie a reflector 121 which may be any type of reflective surface. This partially transparent material may take the form of a fluid, a gel or a solid. Without limiting the invention we further discuss FIG. 7 using fluid as an example material. To avoid any unnecessary repetition, like reference numerals are used to denote like features.

In this example, light is emitted from light source 3 and enters photonic chip 1. The light passes through coupler 1 and is coupled to the first waveguide 5 and the second waveguide 7. In this example, the coupler 1 is a directional coupler of the type shown in FIG. 3. However, other types of couplers could be used, for example, but not limited to the couplers of FIGS. 4 and 5.

In this example, the test area 11 is a fluid with an unknown refractive index, which will be referred to as n+dn. A mirror 121 is provided behind the fluid in test area 11 such that light exits the first waveguide 7 is passed through the fluid, is reflected by the mirror 121, passes though the fluid again and it coupled back into the first waveguide. The reference area 13 is a fluid with known refractive index n. A mirror 121 is provided behind the fluid in test area 11 such that light exits the second waveguide 7 is passed through the fluid, is reflected by the mirror 121, passes though the fluid again and it coupled back into the second waveguide 7. Calibrating this device with two fluids of the same refractive index, such that the light in the output waveguide is minimised, leads to the highest sensitivity when the refractive index in the test area is allowed to change by a small value, dn.

Devices in accordance with the above embodiment may find applications in sensing the small change in refractive index of a fluid, such as when sugar is added to water. In this case, food and pharmaceuticals companies have a need to determine the sugar content to the highest accuracy. In other applications, inhibitors introduced to coolant liquids must be determined to high accuracy. The channels that hold the fluid may be part of an optofluidic chip through which the fluid travels or an etched section of the photonic chip into which the fluid may flow, and partially overlap with the first 5 and second 7 waveguide.

Devices in accordance with further embodiments may be used to measure a small change in light scattered by a data storage medium. Examples include the compact disc where the data is stored as an indentation in a metal film, and CD-R where the refractive index of a dye in the pixel is changed or a CD-RW where the physical state of a material is changed. Devices in accordance with embodiments are particularly well suited to sensing a small physical changes within a small area (pixel) and thus may offer advantages in optically reading stored data. In one embodiment the device may measure the pixel in a binary way (0 for low index, 1 for high index) or alternatively it may measure a series of increments in the refractive index change.

Figure 8:
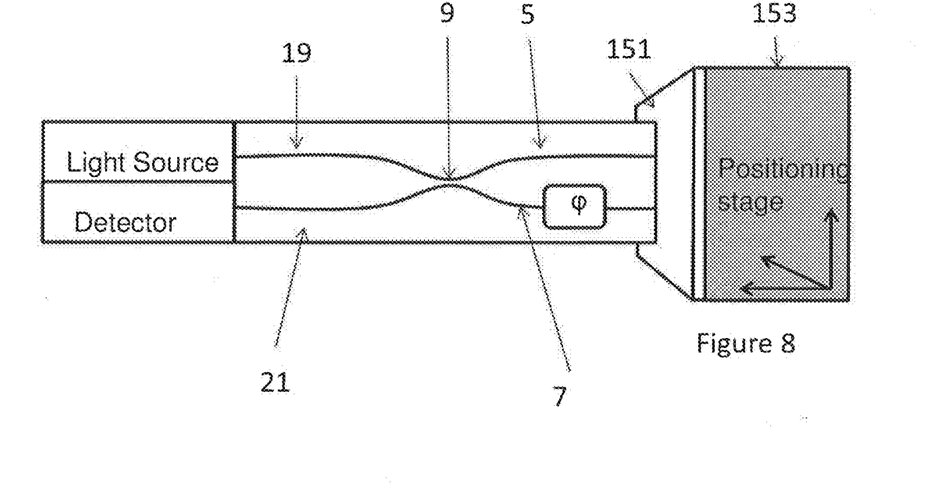
FIG. 8 is schematic diagram of a device for measuring the difference the optical thickness of a sample as it is scanned in the plane perpendicular to the propagation direction of light.

FIG. 8 is a device in accordance with a further embodiment and shows a sample 151 mounted at the ends of the first 5 and second 7 waveguides on positioning stage 153. The part of the sample 151 at the end of the first waveguide 5 is the first region and the part of the sample at the end of the second waveguide is the second region. Here, the device instead of measuring a variation between a test area and a reference measures a variation between 2 parts or regions of the same sample. The sample may be scanned over its surface to enable mapping of small changes in the sample optical thickness: that is, its thickness or refractive index. In one embodiment the sample area would be of greater extent than the spacing of the waveguide spacing so the map would reveal an image of the difference in signal at the outputs of the first 5 and second 7 waveguides. Positioning of the sample could be achieved by the shown xyz stage 153 allowing linear displacement of the sample or a rotating stage with linear displacement along the radius may be more suitable for probing a disc type area.

A positioning system is drawn to show the motion of the sample, but an identical effect could be achieved by moving the photonic chip relative to the sample.

Figure 9:
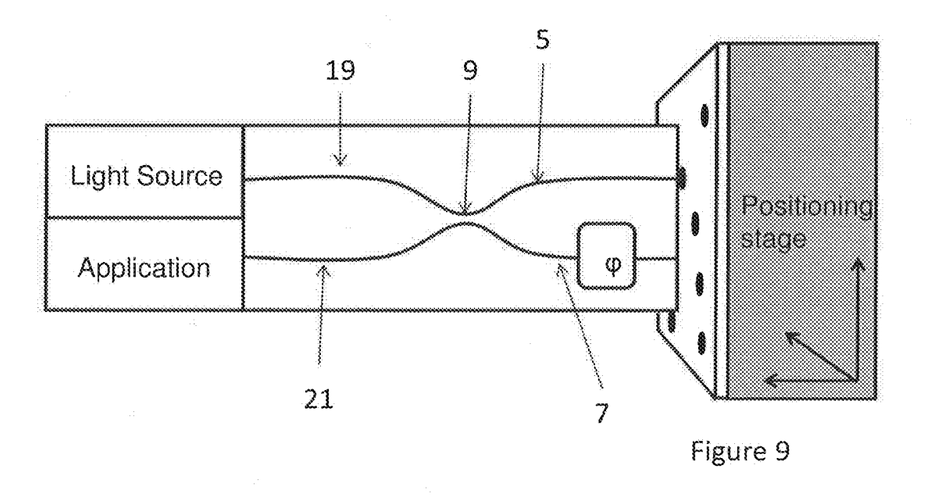
FIG. 9 is schematic diagram of a device for measuring the emission from an optically active defect in a sample.

FIG. 9 shows a variation on sample of FIG. 8. Here, the sample contains single emitters, such as single quantum dots, colour centres in diamond, dye molecules or any other optically active defects. In this case the light injected into the Input waveguide 19 may be prevented from reaching the output waveguide. However, fluorescence or luminescence from the single emitter located in the path of the first waveguide 5 is free to be guided from the first waveguide 5 to the output waveguide 21. Thus the light exiting the output waveguide consists mainly of the emission from the Test Area 11, the light from the light source having been filtered out by destructive interference. In the field of quantum photonics the light from the test area 11 may have favourable properties such as quantum statistics, narrow spectral properties or be entangled so it will be advantageous for applications in quantum optics.

In this case the light may be detected as shown in FIG. 1, or passed onto some Application. Examples include a photonic quantum information processing device, quantum communication system, photonic sensor system or quantum random number generator.

In practical applications it may be advantageous to mount the device containing the quantum emitter on Positioning stage (FIG. 9) so it may be optimally aligned for 1 defect or quantum dot to interact with light from the first waveguide. By scanning the Positioning stage this will enable mapping of small changes in the sample. The emitter could equally be located to interact with light in the guide Y. An optimal choice of reflection/transmission coefficient of the coupler 1 may be required to maximise the fluorescence/luminescence of the emitter reaching the detector.

Figure 10:
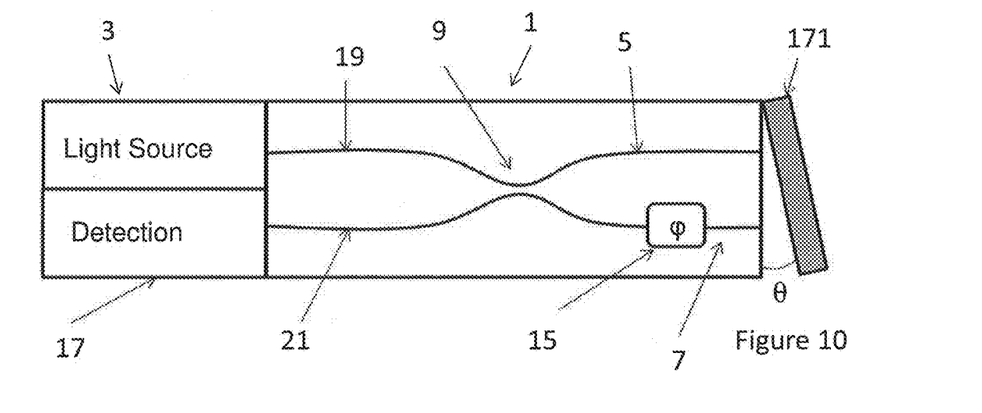
FIG. 10 is schematic diagram of the device to measure the small displacement of a reflecting surface at the outputs.

FIG. 10 shows a device in accordance with a further embodiment that may be used to measure small deflections of a mechanical system 171. To avoid any unnecessary repetition, like reference numerals will be used to denote like features. Any small rotation of the mechanical system, shown by the angle θ, at the output of the first waveguide 5 and the second waveguide 7 would change the relative phases of the light reflected back to the output waveguide 21. In the example shown the light in the first waveguide 5 would experience a reduced path length relative to light the second waveguide. The device can therefore be ensure that a mechanical system is level or exactly parallel with respect to photonic chip 4. Alternatively, it may be used to measure small deviations in angle θ as the mechanical system vibrates.

An example is a flexible micromechanical device located at the outputs of the first waveguide and the second waveguide which is able to move with the photonic chip moves: thus small mechanical motions of the system can be measured. Such a miniaturised system has many uses in sensing motion such as in air airbag triggers, aerospace etc. Such a device can be made small, using microelectromechanical system (MEMS) manufacturing techniques it can measure displacements in position at a fraction of a wavelength of the light used.

In a further embodiment, the device can be used to sense displacement of a rotating axis, such as in an engine, which is an early indicator of failure. In this case the rotating component would be positioned at the output of the first waveguide 5 and the second waveguide 7, and provided that the rotating component rotates about a fixed axis, the signal reflected by the axis may be constant. As the rotating component starts to wobble (for instance through failure of bearings) this would translate to a change in the reflected signal into the output waveguide. The device could operate in a high temperature or high pressure environment over a long time, subject to the stability of the component parts.

Figure 11:
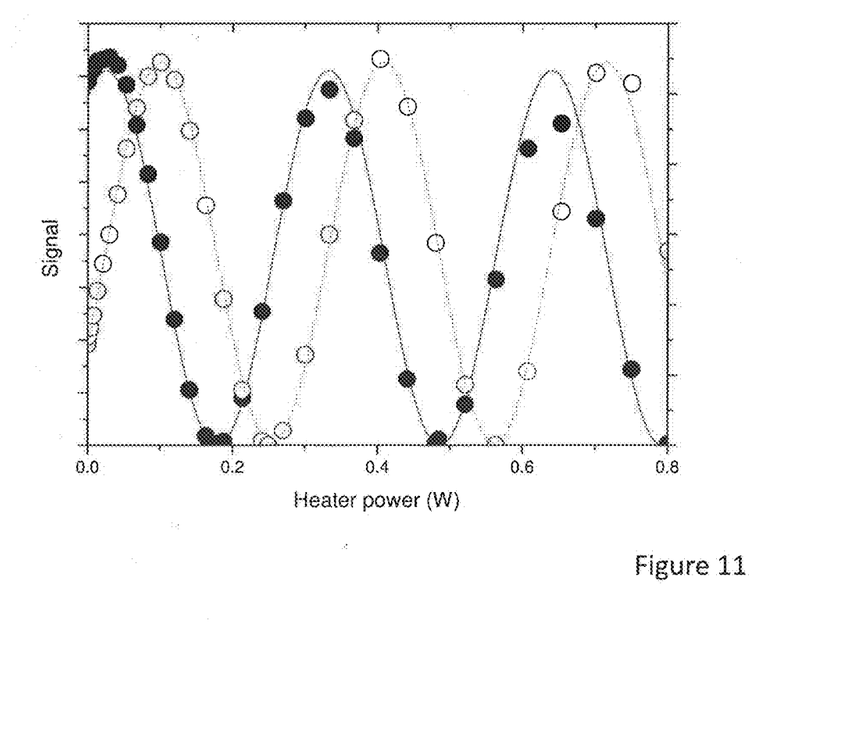
FIG. 11 is experimental data showing the variation in signal as a function of the controllable phase as a sample at the output facets of the device is tilted by a small angle. As can be seen the small rotation is detectable as a large change in the intensity.

FIG. 11 shows preliminary experimental data from a measurement with an arrangement similar to that of FIG. 10. In this case a mirror was located in the test and reference areas of the device, which was attached to the 6-axis micropositioning stage capable of rotating the mirror as shown in FIG. 10. Solid data points show the light intensity detected in the output guide 21 as a function of the phase shift provided by a heater element in the second waveguide, when the mirror is close to being parallel to the output facet of the photonic chip 1. The open datapoints show a similar set of data when the tilt angle of the mirror θ is changed by 0.027 degrees. In this case the change in Signal at a heater power of, for example 0.18 W is more than a factor 1000 showing the extreme sensitivity of devices in accordance with embodiments. Any small variation in the rotation will be shown as a large variation in signal at the detector 17.

Figure 12:
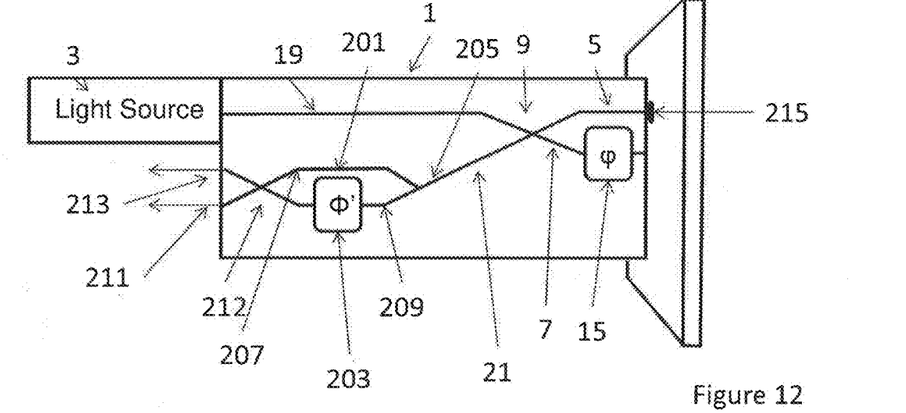
FIG. 12 is a schematic diagram of a device for directing the emission of an optically active defect into an interferometer.

FIG. 12 shows a device in accordance with an embodiment where the addition of a Mach-Zender interferometer (MZI) 201 with a MZI phase shift element, $\phi'$ 203 in one arm can be used to increase the functionality of the device. In the device shown in FIG. 12, like reference numerals are used to denote like features. The MZI 201 is placed in the output waveguide 21. These inputs are directed into first MZI coupler 205 that couples the input signals to first MZI arm 207 or a second MZI arm. In this figure, the MZI phase shift element 203 is located in the second MZI arm 209, but it could also be located in the second MZI arm 209. The first 207 and second 209 MZI arms are then coupled at second MZI coupler 212 to output the signal into first 211 and second 213 MZI outputs. Which of the MZI outputs is selected can be controlled by the MZI phase shift element 203.

As with FIG. 9 the phase shift element 15 is set to suppress the emission from the light source 3 that enters into the output guide 21, but the emission from the single quantum emitter is able to do so subject to the transmission loss of the coupler 1. In this case the MZI may be set such that the emission from the single quantum emitter 215, located at the end of the first guide is shared between the two MZI outputs 211, 213. Autocorrelation measurements with two single photon detectors at these outputs 211, 213 can verify the quantum statistics of the single quantum emitter 215. Alternatively, the MZI phase shift element 203 $\phi'$ may be used to switch which output 211, 213 the photon is directed to. The outputs 211, 213 may be passed to another application on the same photonic chip or off the chip though fibres to some other application.

Figure 13:
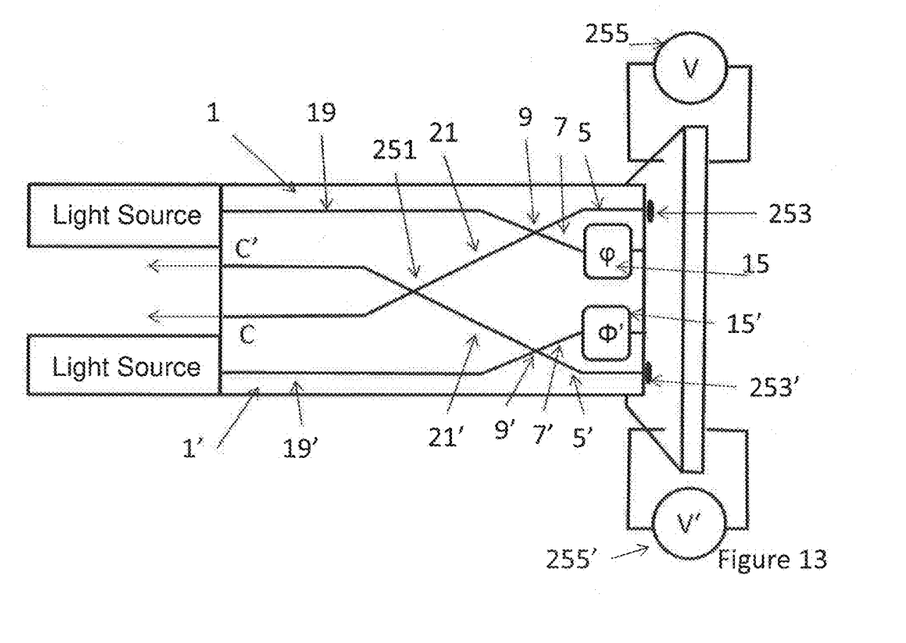
FIG. 13 is a schematic diagram of a photon chip comprising two optical measuring devices configured to interfere the output from two optically active defects.

FIG. 13 shows a device similar to that shown in FIG. 9. In this case, there are two optical measuring devices provided on a single chip, the output guides of which are coupled together. For convenience, the chip will be described as it appears on the paper. A first optical measuring device is provided with an input waveguide 19, an output waveguide 21, a first waveguide 5 and a second waveguide 7 as previously described. A phase adjusting element 15 is provided in the second waveguide 7, but could just as easily be provided in the first waveguide 5. The first waveguide 5 is provided such that it collects radiation emitter by first quantum emitter 253.

A second optical measuring device is provided parallel to the first optical measuring device. The second optical measuring device 1' is provided with an input waveguide 19', an output waveguide 21', a first waveguide 5' and a second waveguide 7' as previously described. A phase adjusting element 15' is provided in the second waveguide 7', but could just as easily be provided in the first waveguide 5'. The first waveguide 5' is provided such that it collects radiation emitter by second quantum emitter 253'.

The two output waves 21, 21' from the first 1 and second 1' optical measuring devices cross at a balanced coupler 251 to realise two photon interference from the photons emitted from the two quantum emitters 253, 253'. Provided both quantum emitters 253, 253' are emitting at the same energy, interference at the coupler 251 will result in the output state after the coupler $|2_C 0_{C'}\rangle + |0_C 2_{C'}\rangle$, that is a 2-photon "NOON" state. This state is of particular interest for some applications in quantum photonics due to its enhanced sensitivity to phase changes, and thus can be used for quantum-enhanced sensing.

Achieving two single photon emitters at the same wavelength can be achieved in some material systems by careful sample preparation (for instance, Silicon-Vacancy defects in diamond) or by post-growth control of the emission energy by some tuning mechanism, for example Stark-shifting the emission of single quantum dots by embedding them in independent diode structures which may be controlled by voltages, V 255 and V' 255'.

While certain embodiments have been described, these embodiments have been presented by way of example only, and are not intended to limit the scope of the inventions. Indeed the novel methods and devices described herein may be embodied in a variety of other forms; furthermore, various omissions, substitutions and changes in the form of methods and devices described herein may be made without departing from the spirit of the Inventions. The accompanying claims and their equivalents are intended to cover such forms of modifications as would fall within the scope and spirit of the inventions.

The invention claimed is:

1. An optical measuring device for measuring a measurement region, the optical device comprising:
   a photonic chip with an interferometer defined on said chip, said interferometer comprising:
   a first waveguide;
   a second waveguide; and
   an interference region,
   wherein the first and second waveguides carry signals from the interference region to the measurement region and back to the interference region, a signal in the first waveguide being reflected back to the interference region from a first region of the measurement region and a signal in the second waveguide being reflected back to the interference region from a second region of the measurement region,
   the optical device being configured to measure an optically activated quantum emitter in the measurement region such that the quantum emitter is coupled to one of the first or second waveguide, the optical device further comprising:
   a phase adjuster configured to provide a phase difference between the signals in the first and second waveguides reflected by the measurement region, wherein the phase adjuster includes one of: a heating element configured to heat a part of at least one of the first and second waveguides, a strain inducing element configured to apply a force to a part of at least one of the first and second waveguides, and an electric field generator configured to apply an electric field to a part of at least one of the first and second waveguides;

a controller, configured to control the phase adjuster; and an output waveguide defined on said photonic chip and configured to carry a signal from the interference region after it has been reflected by the measurement region, the amount of signal transferred to the output waveguide being controlled by the phase adjuster and the controller, the phase adjuster and the controller being configured to set a phase difference between the signals in the first and second waveguide to minimize the signal transferred from the input waveguide to the output waveguide such that a signal from the quantum emitter can be observed, and the optical measuring device further comprising a positioning stage configured to align the optically activated quantum emitter to interact with light from the first or second waveguide.

2. An optical measuring device according to claim 1, further comprising:

an input waveguide adapted to pass a light signal to said interference region such that the light signal propagates along the first and second waveguides after the interference region.

3. An optical measuring device according to claim 1, wherein a detector is provided to receive the output from the output waveguide.

4. An optical measuring device according to claim 1, wherein the measurement region comprises a sample having a surface, and wherein the surface of the sample is orthogonal to the direction of travel of the signal in the first and second waveguides.

5. An optical measuring device according to claim 1, wherein the first and second waveguides are single mode waveguides.

6. An optical measuring device according to claim 1, wherein a light source is attached to the input waveguide.

7. An optical measuring device according to claim 1, wherein the phase adjuster on said photonic chip is a heating element configured to heat part of the first and/or second waveguide.

8. An optical measuring device according to claim 1, wherein the light signal provided from the input waveguide is at an energy that can excite the quantum emitter.

9. An optical measuring device according to claim 8, wherein the output waveguide is coupled to a further photonic circuit.

10. An optical measuring system comprising:
a first optical measuring device; and
a second optical measuring device,
the first optical measuring device comprising the optical measuring device of claim 8 and the second optical measuring device comprising the optical measuring device of claim 8, wherein the output guide of the first optical measuring device and the output guide of the second optical measuring device are coupled at a coupler.

11. An optical measuring device for measuring a measurement region, the optical device comprising:

a photonic chip with an interferometer defined on said chip, said interferometer comprising:
a first waveguide;
a second waveguide; and
an interference region;
wherein the first and second waveguides carry signals from the interference region to the measurement region and back to the interference region, a signal in the first waveguide being reflected back to the interference region from a first region of the measurement region and a signal in the second waveguide being reflected back to the interference region from a second region of the measurement region;

the optical device further comprising:
a phase adjuster configured to provide a phase difference between the signals in the first and second waveguides reflected by the measurement region, wherein the phase adjuster includes one of: a heating element configured to heat a part of at least one of the first and second waveguides, a strain inducing element configured to apply a force to a part of at least one of the first and second waveguides, and an electric field generator configured to apply an electric field to a part of at least one of the first and second waveguides;

a controller, configured to control the phase adjuster;
an output waveguide defined on said photonic chip and configured to carry a signal from the interference region after it has been reflected by the measurement region, the amount of signal transferred to the output waveguide being controlled by the phase adjuster and the controller, the controller being configured to control the phase adjuster to minimize the output signal in the output waveguide, wherein the controller is further configured to determine the phase adjustment applied for minimizing the signal in the output waveguide.

12. A method of performing an optical measurement of a measurement region, the method comprising:

providing an optical measuring device comprising a photonic chip with an interferometer defined on said chip, said interferometer comprising a first waveguide, a second waveguide and an interference region;

passing signals from the interference region via said first and second waveguides to the measurement region and back to the interference region via the first and second waveguides, a signal in the first waveguide being reflected back to the interference region from a first region of the measurement region and a signal in the second waveguide being reflected back to the interference region from a second region of the measurement region;

passing a signal from the interference region after it has been reflected by the measurement region along an output waveguide defined on said photonic chip;

varying a phase difference between the signals in the first and second single waveguides reflected by the measurement region to minimize the output signal in the output waveguide; and determining the phase adjustment applied for minimizing the signal in the output waveguide.

13. A method of performing an optical measurement of a measurement region, the method comprising:

providing an optical measuring device comprising a photonic chip with an interferometer defined on said chip, said interferometer comprising a first waveguide, a second waveguide and an interference region, the optical device being configured to measure an optically activated quantum emitter in the measurement region such that said quantum emitter is coupled to one of the first or second waveguide;

aligning the optically activated quantum emitter to interact with light from the first or second waveguide using a positioning stage;

passing signals from the interference region via said first and second waveguides to the measurement region and back to the interference region via the first and second waveguides, a signal in the first waveguide being reflected back to the interference region from a first region of the measurement region and a signal in the second waveguide being reflected back to the interference region from a second region of the measurement region;

passing a signal from the interference region after it has been reflected by the measurement region along an output waveguide defined on said photonic chip; and setting a phase difference between the signals in the first and second single waveguides reflected by the measurement region to minimize the signal transferred from the input waveguide to the output waveguide such that a signal from the quantum emitter can be observed.

* * * * *